United States Patent
Bizup

(12) 
(10) Patent No.: US 9,149,621 B2
(45) Date of Patent: Oct. 6, 2015

(54) COLLET LOCK

(75) Inventor: Raymond Bizup, Feasterville, PA (US)

(73) Assignee: MEDICAL COMPONENTS, INC., Harleysville, PA (US)

( * ) Notice: Subject to any disclaimer, the term of this patent is extended or adjusted under 35 U.S.C. 154(b) by 150 days.

(21) Appl. No.: 13/206,565

(22) Filed: Aug. 10, 2011

(65) Prior Publication Data

US 2012/0041426 A1    Feb. 16, 2012

Related U.S. Application Data

(60) Provisional application No. 61/372,260, filed on Aug. 10, 2010.

(51) Int. Cl.
  *A61M 39/02* (2006.01)
  *A61M 39/10* (2006.01)

(52) U.S. Cl.
  CPC ....... *A61M 39/0208* (2013.01); *A61M 39/1011* (2013.01); *A61M 2039/0229* (2013.01); *A61M 2039/1027* (2013.01)

(58) Field of Classification Search
  CPC .......... A61M 2020/006; A61M 5/344; A61M 39/00; A61M 39/10; A61M 39/0208; A61M 39/1011; A61M 2039/0229; A61M 2039/1016; A61M 2039/1027
  USPC ......... 604/533, 326, 536, 535, 103, 513, 539, 604/103.01
  See application file for complete search history.

(56) References Cited

U.S. PATENT DOCUMENTS

| 2,874,981 A | * | 2/1959 | Brady ........................... 285/238 |
| 3,244,437 A | | 4/1966 | Belicka et al. |
| 3,456,965 A | | 7/1969 | Gajewski et al. |

(Continued)

FOREIGN PATENT DOCUMENTS

| EP | 0976418 B1 | 10/2004 |
| FR | 2703593 A1 | 10/1994 |

(Continued)

OTHER PUBLICATIONS

International Application No. PCT/US08/067515, International Preliminary Report on Patentability, dated Dec. 22, 2009, 9 pages.

(Continued)

*Primary Examiner* — Edelmira Bosques
(74) *Attorney, Agent, or Firm* — Buchanan Ingersoll & Rooney PC

(57) ABSTRACT

A locking apparatus for connecting a catheter to a stem. The locking apparatus comprises a collet sleeve, which includes an annular wall defining a center channel and a plurality of resilient prongs protruding inwardly into a portion of the center channel. The locking apparatus also comprises a lockable insert, which includes an annular wall defining a center channel. The center channel of the lockable insert is coaxial with the center channel of the collet sleeve. The lockable insert is configured to be placed at a first locking position in which the annular wall of the lockable insert asserts no or minimal radial compression against the plurality of the resilient prongs of the collet sleeve, and the lockable insert is further configured to be moved to a second locking position in which the annular wall of the lockable insert radially compresses the plurality of the resilient prongs of the collet sleeve.

9 Claims, 4 Drawing Sheets

(56) References Cited

U.S. PATENT DOCUMENTS

| | | |
|---|---|---|
| 4,405,163 A | 9/1983 | Voges et al. |
| 4,704,103 A | 11/1987 | Stöber et al. |
| 4,723,948 A | 2/1988 | Clark et al. |
| 4,744,788 A | 5/1988 | Mercer, Jr. |
| 4,762,517 A | 8/1988 | McIntyre et al. |
| 4,778,452 A | 10/1988 | Moden et al. |
| 4,820,288 A * | 4/1989 | Isono ................. 604/534 |
| 4,929,236 A * | 5/1990 | Sampson ............ 604/175 |
| 4,943,091 A * | 7/1990 | Bartholomew ......... 285/12 |
| 5,137,524 A * | 8/1992 | Lynn et al. ............ 604/533 |
| 5,185,003 A | 2/1993 | Brethauer |
| 5,213,574 A | 5/1993 | Tucker |
| 5,240,289 A | 8/1993 | Gottling et al. |
| 5,360,407 A | 11/1994 | Leonard et al. |
| 5,399,168 A | 3/1995 | Wadsworth, Jr. et al. |
| 5,437,650 A * | 8/1995 | Larkin et al. ........... 604/536 |
| 5,637,102 A | 6/1997 | Tolkoff et al. |
| 5,833,654 A | 11/1998 | Powers et al. |
| 5,848,989 A | 12/1998 | Villani |
| 6,003,906 A | 12/1999 | Fogarty et al. |
| 6,113,572 A | 9/2000 | Gailey et al. |
| 6,155,610 A | 12/2000 | Godeau et al. |
| 6,183,465 B1 * | 2/2001 | Meier et al. ........... 604/535 |
| 6,221,064 B1 | 4/2001 | Nadal |
| 6,971,390 B1 | 12/2005 | Vasek et al. |
| 6,976,980 B2 | 12/2005 | Brenner et al. |
| 2005/0084327 A1 | 4/2005 | Chelchowski et al. |
| 2007/0219510 A1 | 9/2007 | Zinn et al. |
| 2007/0270770 A1 | 11/2007 | Bizup |
| 2007/0276356 A1 | 11/2007 | Downing et al. |
| 2008/0097296 A1 | 4/2008 | Pepin |

FOREIGN PATENT DOCUMENTS

| | | |
|---|---|---|
| FR | 2776747 A1 | 10/1999 |
| SE | 463116 B | 8/1990 |
| WO | 2004002555 A1 | 1/2004 |
| WO | 2006004943 A2 | 1/2006 |

OTHER PUBLICATIONS

International Application No. PCT/US08/067515, International Search Report, mailed Sep. 5, 2008, 3 pages.

International Application No. PCT/US08/067515, Written Opinion, dated Dec. 19, 2008, 8 pages.

International Application No. PCT/US08/067527, International Preliminary Report on Patentability, dated Mar. 3, 2011, 6 pages.

International Application No. PCT/US08/067527, International Search Report, mailed Sep. 5, 2008, 5 pages.

International Application No. PCT/US08/067527, Written Opinion, dated Dec. 19, 2009, 8 pages.

International Application No. PCT/US11/047157, International Search Report, mailed Dec. 7, 2011, 2 pages.

International Application No. PCT/US11/047157, Written Opinion, mailed Dec. 7, 2011, 5 pages.

"R Port Implantable Vascular Access System Instructions for Use", Brochure, Therex Corporation (1994), 8 pages.

"stem." Compact Oxford English Dictionary. 2009. AskOxford. <http://www.askoxford.com/concise_oed/stem_1?view=uk>.

* cited by examiner

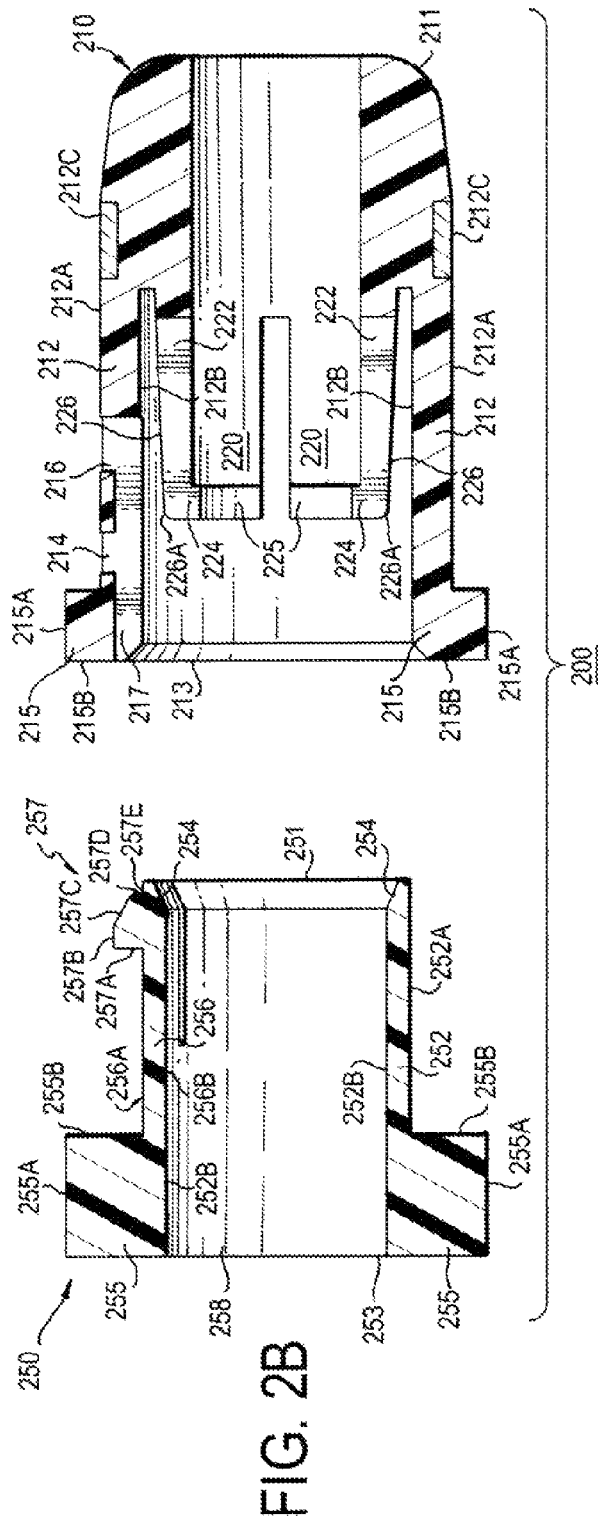
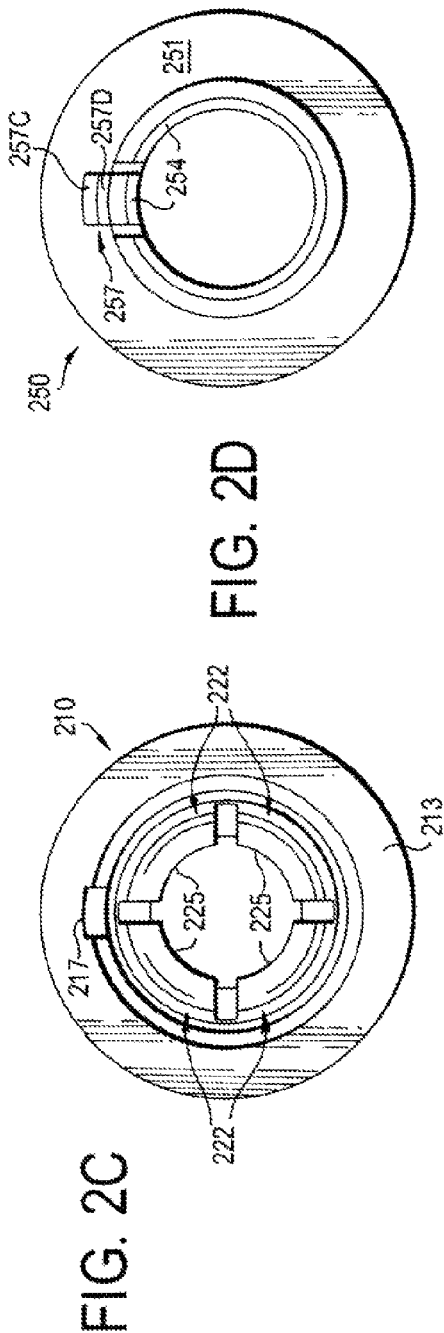
FIG. 2B
FIG. 2C
FIG. 2D

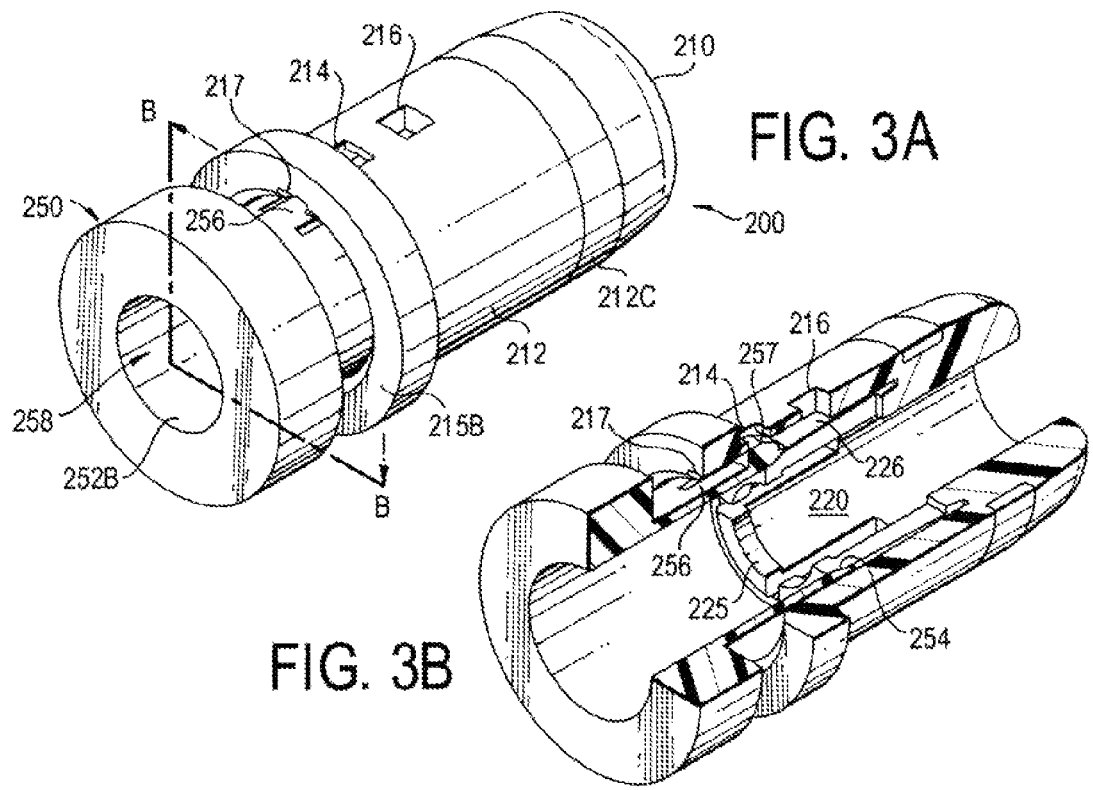
FIG. 3A
FIG. 3B
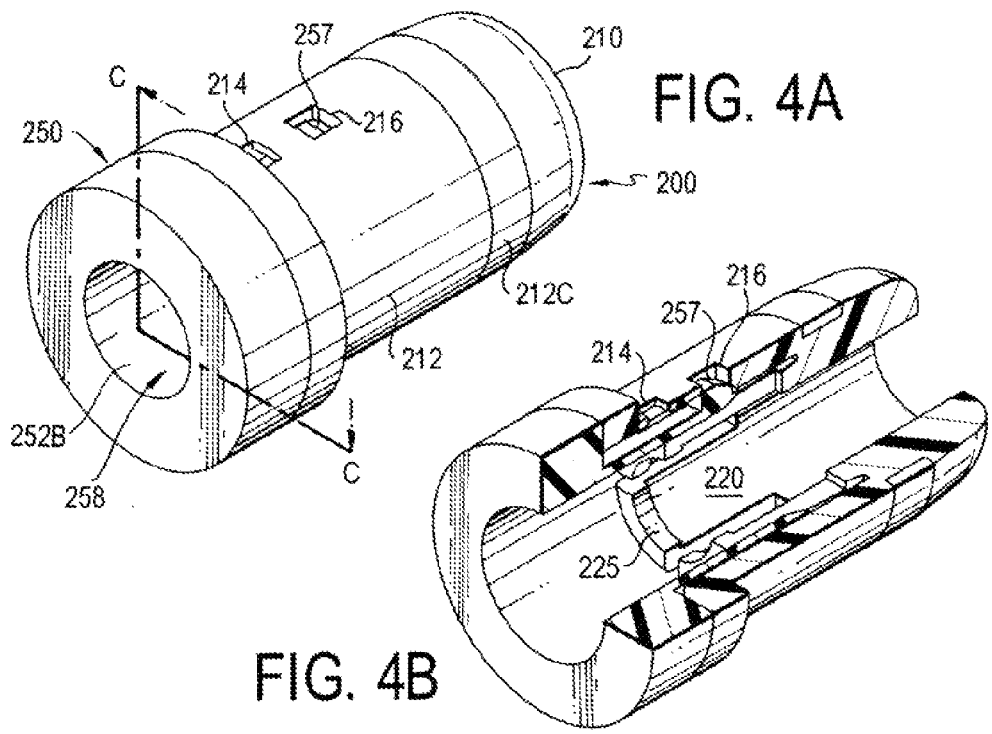
FIG. 4A
FIG. 4B

COLLET LOCK

CROSS REFERENCE TO RELATED APPLICATION

This application claims priority to U.S. Provisional Patent Application No. 61/372,260, entitled "Collet Lock" and filed Aug. 10, 2010, the contents of which application are incorporated herein by reference.

FIELD OF THE INVENTION

The present invention relates to a locking apparatus and, more specifically, to a locking device for connecting a catheter to an outlet stem, such as an outlet stem of an implantable port.

BACKGROUND OF THE INVENTION

Implantable vascular access ports are used extensively in the medical field to facilitate the performance of recurrent therapeutic tasks. A typical access port comprises a needle-impenetrable housing having a fluid reservoir that is sealed by a needle penetrable septum. The access port also includes an outlet stem which projects from the housing and provides a fluid passageway that communicates with the fluid reservoir. The outlet stem is used to couple the housing to a catheter. Specifically, the vascular access port is attached to the proximal end of the catheter. The distal end of the catheter is placed into a vessel. The access port is generally implanted subcutaneously at a location that is easily accessible.

Once the vascular access system is implanted, a non-coring needle, e.g., a Huber needle, attached to a feed line may be used to access the implanted vascular access port, by penetrating the septum, to deliver a desired medication. Alternatively, bodily fluids can be withdrawn from the location where the distal end of the catheter is placed.

During the implantation procedure for a typical implantable access port having a single reservoir, a subcutaneous pocket is first created to receive and house the access port. This is done by making an incision in the skin of the patient at the intended implantation site for the access port. The access port is then inserted beneath the skin through the incision. The outlet stem of the access port is usually received within the pocket last, after the proximal end of the access port is placed in the subcutaneous pocket. A catheter is first placed at a desired location within the patient and then coupled to the outlet stem of the access port. The coupling of the catheter to the outlet stem of the access port generally uses a locking apparatus.

SUMMARY OF THE INVENTION

In accordance with an aspect of an exemplary embodiment of the present invention there is provided a locking apparatus for connecting a catheter to a stem of an implantable access port. The locking apparatus includes a collet sleeve and a lockable insert. The collet sleeve has a first end, a second end, an annular wall, and at least one resilient prong. The annual wall defines a center channel extending from the first end to the second end of the collet sleeve. The at least one resilient prong protrudes inwardly from the first end and extends into a portion of the center channel of the collet sleeve. The at least one resilient prong comprises a gripping surface facing the center channel. The lockable insert has a first end, a second end, and an annular wall defining a center channel extending from the first end to the second end of the lockable insert. The center channel of the lockable insert is coaxial with the center channel of the collet sleeve. The lockable insert is configured to be placed at a first locking position at which the annular wall of the lockable insert asserts no or minimal radial compression against the at least one resilient prong of the collet sleeve. The lockable insert is further configured to be moved to a second locking position at which the annular wall of the lockable insert radially compresses the at least one resilient prong of the collet sleeve.

In accordance with another aspect of an exemplary embodiment of the present invention there is provided a locking apparatus for connecting a catheter to a stem of an implantable access port. The locking apparatus includes a collet sleeve and a lockable insert. The collet sleeve has a first end, a second end, an annular wall, and a gripping means. The annual wall defines a center channel extending from the first end to the second end of the collet sleeve. The lockable insert has a first end, a second end, and an annular wall defining a center channel extending from the first end to the second end of the lockable insert. The center channel of the lockable insert is coaxial with the center channel of the collet sleeve. The gripping means is for being in an open state for not compressing the catheter against the stem and in a closed state for compressing the catheter against the stem. The lockable insert is configured to be placed at a first locking position at which the gripping means is in the open state. The lockable insert is further configured to be moved to a second locking position at which the annular wall of the lockable insert engages the gripping means and the gripping means is in the closed state.

BRIEF DESCRIPTION OF THE DRAWINGS

For the purpose of illustration, there are shown in the drawings certain embodiments of the present invention. In the drawings, like numerals indicate like elements throughout. It should be understood, however, that the invention is not limited to the precise arrangements, dimensions, and instruments shown. In the drawings:

FIG. 2B is a view of a cross section of the locking apparatus illustrated in FIG. 1 taken along a line A-A illustrated in FIG. 2A, in accordance with an exemplary embodiment of the present invention;

FIG. 2C is a view of an end of the collet sleeve illustrated in FIG. 2A, in accordance with an exemplary embodiment of the present invention;

FIG. 2D is a view of an end of the lockable insert illustrated in FIG. 2A, in accordance with an exemplary embodiment of the present invention;

FIG. 3A is a perspective view of the locking apparatus illustrated in FIG. 2A, in which the lockable insert is positioned at a first location, in accordance with an exemplary embodiment of the present invention;

FIG. 3B is a cut-out view of the locking apparatus illustrated in FIG. 3A, in accordance with an exemplary embodiment of the present invention;

FIG. 4A is a perspective view of locking apparatus illustrated in FIG. 2A, in which the lockable insert is positioned at a second location, in accordance with an exemplary embodiment of the present invention;

FIG. 4B is a cut-out view of the locking apparatus illustrated in FIG. 4A, in accordance with an exemplary embodiment of the present invention.

DETAILED DESCRIPTION OF THE INVENTION

A catheter-to-stem locking apparatus desirably provides a secure connection between a catheter and an outlet stem, such as an outlet stem of an access port. It is also desirable for the locking apparatus to be easy to operate with gloved hands during an implantation procedure and to provide a positive indication when the catheter is firmly attached to the outlet stem.

Figure 1:
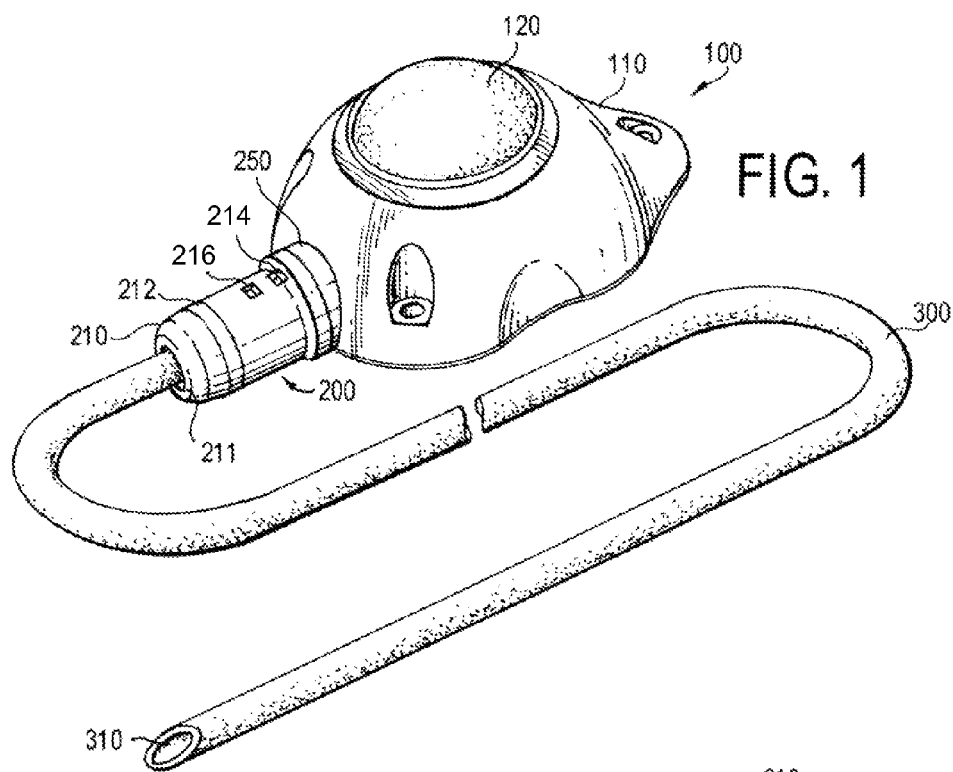
FIG. 1 is a perspective view of an implantable port connected to a catheter using a locking apparatus, in accordance with an exemplary embodiment of the present invention.

Referring to FIG. 1, there is illustrated an exemplary implantable port 100 connected to an exemplary catheter 300 by an exemplary locking apparatus 200, in accordance with an exemplary embodiment of the present invention. The exemplary implantable port 100 comprises a port body which houses a reservoir capped by a needle penetrable septum 120. The exemplary implantable port 100 further comprises a stem 400 (illustrated in FIGS. 3C and 4C) and a cap 110 which secures the septum 120 to the port body. The stem 400 is in fluid communication with the reservoir.

The implantable port 100 is used to provide intravenous infusions and/or aspirations for the patient in which it is implanted. During an implantation procedure for the implantable port 100, the catheter 300 is first placed at a desired location in a patient's vasculature or another anatomical structure. A subcutaneous pocket is then created to receive and house the port 100. This is done by making an incision in the skin of the patient at the intended implantation site for the access port 100. The port 100 is then inserted beneath the skin through the incision. The outlet stem 400 of the port 100 may be received within the pocket last, after the proximal end of the port 100 opposite the stem 400 is placed in the subcutaneous pocket. The exemplary catheter 300, which has previously been inserted into the vasculature of the patient, is then slipped onto the stem 400 and secured by the locking apparatus 200, in accordance with an exemplary embodiment of the present invention.

In the particular example illustrated in FIG. 1, for the sake of simplicity, the implantable port 100 is shown as a single reservoir port, and the catheter 300 is shown comprising a single lumen 310. It is to be understood that other embodiments of the locking apparatus 200 are contemplated, such that the locking apparatus 200 may be adapted to connect the outlet stem(s) of multi-reservoir implantable ports (e.g., a dual reservoir) to multi-lumen catheters (e.g., a dual lumen catheter).

Figure 2A:
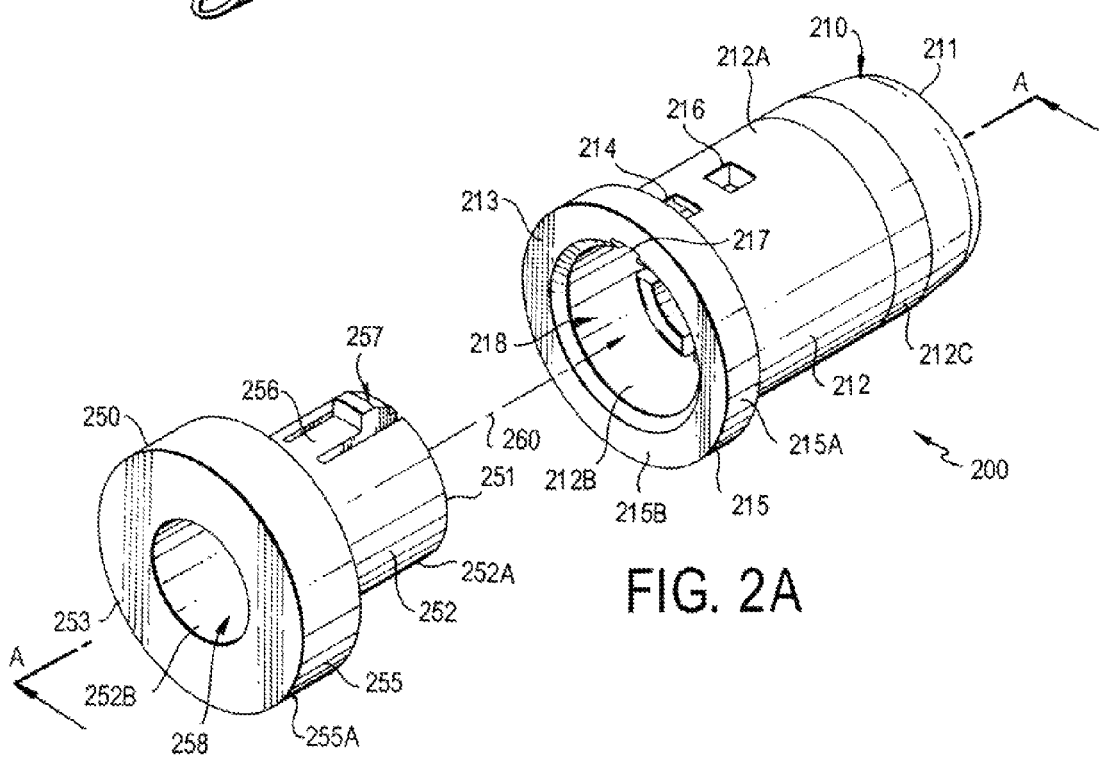
FIG. 2A is an exploded view of the locking apparatus illustrated in FIG. 1, the locking apparatus comprising a collet sleeve and a lockable insert, in accordance with an exemplary embodiment of the present invention.

FIG. 2A is an exploded view of the exemplary embodiment of the locking apparatus 200 illustrated in FIG. 1. FIG. 2B is a view of a cross section of the exemplary embodiment of the locking apparatus 200 taken along a line A-A illustrated in FIG. 2A.

Referring now to FIGS. 2A and 2B together, it is seen that the locking apparatus 200 comprises a collet sleeve 210 and a lockable insert 250. In the particular embodiment illustrated, the collet sleeve 210 comprises a sidewall 212 that has a generally cylindrical or annular shape. Specifically, the sidewall 212 comprises an outer surface 212A that is generally cylindrical in shape and an inner surface 212B that is also generally cylindrical in shape. The inner surface 212B of the sidewall 212 forms a cylindrically shaped center channel 218 extending from a first end 211 to a second end 213 of the collet sleeve 210. The center channel 218 is adapted to receive the stem 400 of the implantable port 100 and the catheter 300. The sidewall 212, the outer and inner surfaces 212A and 212B of the sidewall 212, and the center channel 218 are cylindrical about a central axis 260.

The collet sleeve 210 further comprises an end portion 215 that comprises an outer surface 215A that forms a shortened cylindrical shape and an edge surface 215B. As described above, the outer surface 212A of the collet sleeve 210 forms a cylindrical shape. In fact, the outer surface 212A forms a generally cylindrical shape outside the end portion 215. The outer surface 215A of the end portion 215 comprises an outer diameter greater than the outer diameter of the outer surface 212A. The outer surface 215A is coaxial with the outer and inner surfaces 212A and 212B and the center channel 218 about the central axis 260.

The collet sleeve 210 also comprises a collet 220 deposited inside the center channel 218 of the collet sleeve 210. The collet 220 comprises a plurality of resilient prongs 222, each comprising a taper 226 to a free end 224. Each taper 226 culminates at a rounded edge 226A. Preferably, the plurality of resilient prongs 222 are deposited radially about the center channel 218 of the collet sleeve 210.

In the particular embodiment of the collet sleeve 210 illustrated in FIGS. 2A and 2B, the collet 220 is joined to the inner surface 212B of the sidewall 212 in the center channel 218 closer to the first end 211 of the collet sleeve 210 with the free ends 224 of the resilient prongs 222 pointing toward the second end 213 of the collet sleeve 210. The taper 226 of each resilient prong 222 is on the surface of each prong 222 facing away from the central axis 260 such that an outer diameter of the combined resilient prongs 222 at their free ends 224 is smaller than where the collet 220 joins the inner surface 212B of the sidewall 212. In an exemplary embodiment, the plurality of resilient prongs 222 is integrally formed with the collet sleeve 210.

Each of the free ends 224 of the plurality of resilient prongs 222 comprises a gripping surface 225 which projects radially inwardly from its respective free end 224 toward the central axis 260 of the center channel 218. By projecting radially inwardly, the gripping surfaces 225 are configured to compress against the catheter 300 to lock the catheter 300 in place on the stem 400. Thus, in a closed state, at least a portion of the lockable insert 250 compresses the resilient prongs 222, i.e., the lockable insert 250 and the resilient prongs 222 provide radial compression, as described below. In an open state, the lockable insert 250 does not compress the resilient prongs 222, i.e., the lockable insert 250 and the resilient prongs 222 provide no or minimal radial compression, as described below. The use of the free ends 224 in locking the catheter 300 in place is described in further detail below.

FIG. 2B illustrates a cross section of the gripping surfaces 225. In the portion of the cross section lying in the plane containing the center axis 260, the gripping surfaces are generally raised ledges at the free ends 224 of the resilient prongs 222. More specifically, the cross sections of the gripping surfaces 225 lying in the plane containing the center axis 260 are rectangular in shape and comprise sharp corners. It is to be understood that other shapes of such cross sections of the gripping surfaces 225 are contemplated. For example, in another exemplary embodiment, such cross section of the gripping surfaces 225 may comprise a raised portion of generally curved shape relative to the central axis 260. Such curved shape may take the form of a semicircle that projects radially inwardly toward the central axis 260. In yet another exemplary embodiment, such cross section of the gripping surfaces 225 may comprise multiple ridges. Finally, in still another exemplary embodiment, the free ends 224 of the resilient prongs do not include gripping surfaces 225 that project radially inwardly from the fee ends 224. Rather, the free ends 224, themselves or in combination with at least a portion of the interior surfaces of the resilient prongs 222, are gripping surfaces that serve to grip and lock the catheter 300.

Referring again to FIGS. 2A and 2B together, the collet sleeve 210 further comprises a guiding groove 217 formed in the sidewall 212 at the second end 213 of the collet sleeve 210. The guiding groove 217 is a recess formed in the inner surface 212B of the sidewall 212. Specifically, the guiding groove 217 is a recess that extends into the sidewall 212 from the inner surface 212B toward the outer surface 212A but does not open to the outer surface 212A, except at recesses 214 and 216 in certain embodiments. In the exemplary embodiment illustrated in FIGS. 2A and 2B, the guiding groove 217 is open at the second end 213 of the collet sleeve 210 and extends along a portion of the inner surface 212B in a direction parallel to the center axis 260 and toward the first end 211. It is contemplated that in other embodiments, the guiding groove 217 is not open at the second end 213 of the collet sleeve 210.

The guiding groove 217 includes a first recess 214 and a second recess 216 formed in the sidewall 212 of the collet sleeve 210. In the embodiment illustrated in FIGS. 2A and 2B, the first and second recesses 214 and 216 extend through the sidewall 212 and form openings in the outer surface 212A of the sidewall 212. It is contemplated, however, that in other embodiments the first and second recesses 214 and 216 are recesses of the guiding groove 217 that extend into the sidewall 212 from the inner surface 212B toward the outer surface 212A but do not open to the outer surface 212A.

The lockable insert 250 comprises a sidewall 252 that has a generally cylindrical or annular shape. Specifically, the sidewall 252 comprises an outer surface 252A that is generally cylindrical in shape, and an inner surface 252B that is also generally cylindrical in shape. The inner surface 252B of the sidewall 252 forms a cylindrically shaped center channel 258 extending from a first end 251 to a second end 253 of the lockable insert 250. The sidewall 252, the outer and inner surfaces 252A and 252B of the sidewall 252, and the center channel 258 are cylindrical about the central axis 260. Thus, the sidewall 212 of the collet sleeve 210 is coaxial with the sidewall 252 of the lockable insert 250, and the center channel 218 of the collet sleeve 210 is coaxial with the center channel 258 of the lockable insert 250.

In the particular embodiment shown, the center channel 258 of the lockable insert 250 comprises a generally constant interior diameter from the second end 253 to a point close to the first end 251. The center channel 258 is adapted to receive the stem 400 of the implantable port 100 and the catheter 300. The outer diameter of the outer surface 252A of the lockable insert 250 is adapted to fit in the center channel 218 of the collet sleeve 210. The center channel 258 of the lockable insert 250 (and, therefore, also the inner surface 252B) further incorporates a taper 254 close to the first end 251, where the interior diameter of the center channel 258 gradually expands outward toward the first end 251.

The lockable insert 250 further comprises an end portion 255 that comprises an outer surface 255A that forms a shortened cylindrical shape and an edge surface 255B. As described above, the outer surface 252A of the lockable insert 250 forms a cylindrical shape. In fact, the outer surface 252A forms a generally cylindrical shape outside the end portion 255 and not including the locking tab 257 (described below). The outer surface 255A of the end portion 255 comprises an outer diameter greater than the outer diameter of the outer surface 252A.

The edge surface 255B of the lockable insert 250 is formed to abut the edge surface 215B of the collet sleeve 210 when the lockable insert 250 is fully inserted into the collet sleeve 210. The edge surface 255B and the edge surface 215B act as stop surfaces to prevent further axial movement of the collet sleeve 210 about the lockable insert 250 and the lockable insert 250 into the collet sleeve 210. As can be seen in the figures, the outer diameter of the outer surface 215A of the collet sleeve 210 is approximately equal to the outer diameter of the outer surface 255A of the lockable insert 250. It is to be understood, however, that these outer diameters need not be equal in other embodiments.

In the exemplary embodiment shown, the lockable insert 250 further comprises a locking tab 257 deposited at the free end of a live hinge 256. Specifically, the locking tab 257 is disposed on an outer surface 256A of the live hinge 256. The live hinge 256 also includes an inner surface 256B. The live hinge 256 is formed integrally with and as a single piece with the lockable insert 250. The locking tab 257 comprises a perpendicular surface 257A facing the second end 253 of the lockable insert 250, a top surface 257B that is generally parallel with the central axis 260 of the center channel 258 of the lockable insert 250, a sloped surface 257C facing the first end 251 of the lockable insert 250, and a notch facing the first end 251 of the lockable insert 250. The inner surface 256B of the live hinge includes the sloped surface 254. In an exemplary embodiment, the notch comprises a perpendicular surface 257D and a surface 257E that is generally parallel with the axis of the center channel 258. The surface 275E generally follows the contour of the outer surface 252A of the sidewall 252 at the first end 251 of the lockable insert 250.

The locking tab 257 is aligned with the guiding groove 217 of the collet sleeve 210. The guiding groove 217 and the locking tab 257 are sized so that the locking tab 257 can slide freely along the guiding groove 217. Additionally, the locking tab 257 is sized so that at least a portion of the locking tab fits within the recesses 214 and 216, as described below.

Referring now to FIG. 2C, there is illustrated a view of the second end 213 of the collet sleeve 210, in accordance with an exemplary embodiment of the present invention. FIG. 2C illustrates the guiding groove 217 and the fact that it is open to the second end 213 in the embodiment of the collet sleeve 210 illustrated in FIGS. 2A and 2B. FIG. 2C also illustrates that the exemplary collet sleeve 210 includes at least one resilient prong 222, namely, in this particular embodiment, four resilient prongs 222. It is to be understood that other numbers of resilient prongs 222 are contemplated, including one resilient prong 222 and more than one resilient prong 222, such as three, five, six, and even more resilient prongs 222. As is also illustrated in FIG. 2C, there exists a gap between each resilient prong 222. Such gaps provide clearance for the resilient prongs 222 to be compressed radially inwardly by the lockable insert 250.

Referring now to FIG. 2D, there is illustrated a view of the first end 251 of the lockable insert 250, in accordance with an exemplary embodiment of the present invention. FIG. 2D illustrates the locking tab 257 and the sloped surface 257C and the perpendicular surface 257D thereof. As is illustrated in FIG. 2D, there exists a gap between the locking tab 257 and the sidewall 252 of the lockable insert 250 on either side of the locking tab 257 and the live hinge 256. Such gaps provide for the ability of the live hinge 256 to flex inwardly as the locking tab 257 travels from the first recess 214 along the guiding groove 217 to the second recess 216.

Figure 3C:
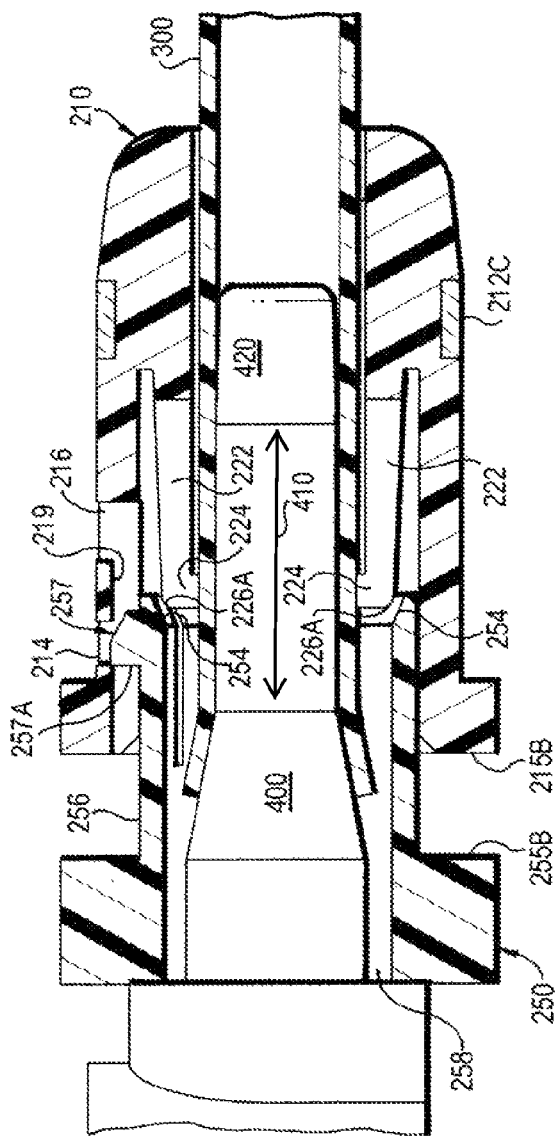
FIG. 3C is a view of a cross section of the locking apparatus taken along a line B-B illustrated in FIG. 3A, in which the locking apparatus is placed over a catheter and a stem, and the lockable insert is positioned at the first location, in accordance with an exemplary embodiment of the present invention.

Referring now to FIGS. 3A, 3B, and 3C, there is illustrated a first locking position of the exemplary locking apparatus 200, in accordance with an exemplary embodiment of the present invention. In this first locking position, the lockable insert 250 is partially placed in the collet sleeve 210. In this particular configuration, the locking tab 257 of the lockable insert 250 is located in the first recess 214 of the collet sleeve 210. The center channel 218 of the collet sleeve 210 is coaxial with the center channel 258 of the lockable insert 250. When the locking tab 257 is in the first recess 214, the lockable insert 250 and the gripping surfaces 225 assert no or minimal radial compression on the resilient prongs 222 of the collet 220. No radial compression includes compression that results in 0 degrees of flex of the prongs 222. Minimal radial compression includes compression that results in less than 1 degree of flex of the prongs 222.

FIG. 3A is an external perspective view of the exemplary locking apparatus 200 in the first locking position. FIG. 3B is a cut out view of the exemplary locking apparatus 200 in the first locking position. Each of the resilient prongs 222 comprises a free end 224 comprising a gripping surface 225 of each prong 222 facing the center channel 218. As can be seen in FIG. 3B, the gripping surface 225 is curved about the central axis 260 of the center channel 218. By being curved, the area of the gripping surface 225 that makes contact with the catheter 300 when it is disposed on the stem 400 of the port 100 is maximized. Preferably, the gripping surfaces 225 of the resilient prongs 222 form a circular configuration about the center channel 218 of the collet sleeve 210.

FIG. 3C is a cross sectional view of the exemplary locking apparatus 200 in the first locking position. The locking apparatus 200 is shown to be placed over the catheter 300 and the stem 400. The lockable insert 250 makes no or minimal contact with the resilient prongs 222 of the collet 220, i.e., there is no or minimal radial compression of the resilient prongs 222 of the collet 220. The resilient prongs 222 are thus in an open position, i.e., the gripping surfaces 225 of the resilient prongs 222 are not pushing against the catheter 300 and a portion 410 of the stem 400, thus allowing the locking apparatus 200 to move freely along the catheter 300 and stem 400.

Additionally, as illustrated in FIG. 3C, the perpendicular surface 257A of the locking tab 257 engages a corresponding perpendicular surface of the first recess 214 preventing the lockable insert 250 from exiting the collet sleeve 210 from the second end 213. Thus, the present invention locking apparatus 200 can be preassembled with the lockable insert 250 located at the first locking position relative to the collet sleeve 210 and shipped as a single unit. The sloped surface 257C of the locking tab 275 and the flexibility of the live hinge 256 make it possible for the locking tab 257, together with the lockable insert 250, to slide out of the first recess 214 and move further into the collet sleeve 210 along the guiding groove 217 to come to rest within the second recess 216.

Figure 4C:
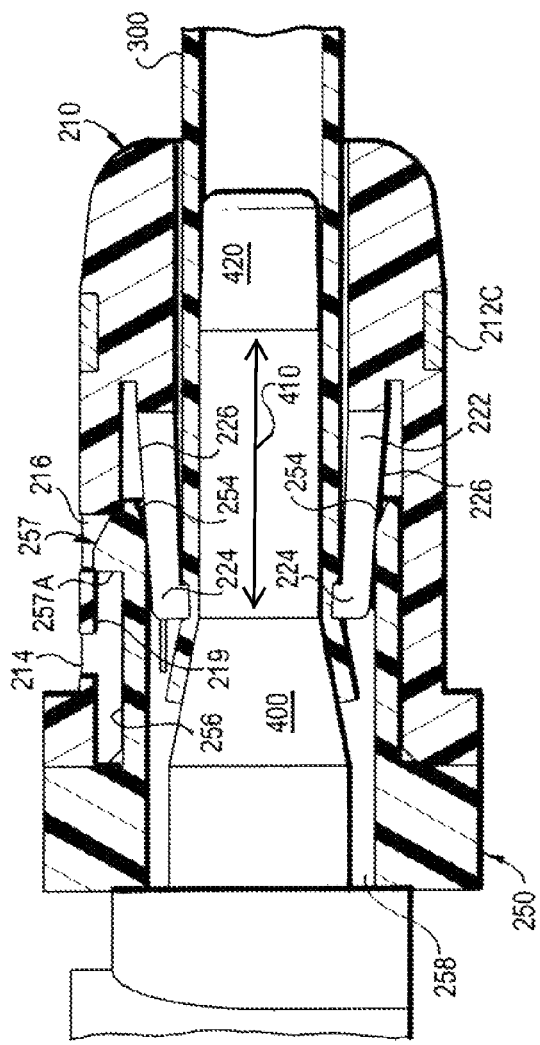
FIG. 4C is a view of a cross section of the locking apparatus taken along a line C-C illustrated in FIG. 4A, in which the lockable insert is positioned at the second location, and the locking apparatus is securing the catheter to the stem, in accordance with an exemplary embodiment of the present invention.

Referring now to FIGS. 4A, 4B, and 4C, there is illustrated a second locking position of the exemplary locking apparatus 200, in accordance with an exemplary embodiment of the present invention. In this second locking position, the lockable insert 250 is fully placed into the collet sleeve 210. In this particular configuration, the locking tab 257 of the lockable insert 250 is located in the second recess 216 of the collet sleeve 210. The center channel 218 of the collet sleeve 210 is coaxial with the center channel 258 of the lockable insert 250. When the locking tab 257 is in the second recess 216, the lockable insert 250 and the gripping surfaces 225 assert radial compression on the resilient prongs 222 of the collet 220. Thus, the resilient prongs 222 are deflected radially inwardly to compress the catheter 300 against the stem 400.

FIG. 4A is an external perspective view of the exemplary locking apparatus 200 in the second locking position. FIG. 4B is a cut out view of the exemplary locking apparatus 200 in the second locking position. The lockable insert 250 is completely inserted into the collet sleeve 210. The locking tab 257 of the lockable insert 250 is located in the second recess 216, and radially compresses the plurality of resilient prongs 222 of the collet 220, causing the plurality of resilient prongs 222 to move inward.

FIG. 4C is a cross sectional view of the exemplary locking apparatus 200 in the second locking position. The locking tab 257 of the lockable insert 250 is located in the second recess 216. The perpendicular surface 257A of the locking tab 257 engages a corresponding perpendicular surface of the second recess 216 securing the lockable insert 250 in this second locking position in relation to the collet sleeve 210 to prevent the lockable insert 250 from backing out.

Additionally, in the second locking position, the edge surface 215B abuts the edge surface 255B preventing further movement of the lockable insert 250 toward the first end 211 of the collet sleeve 210. The notch formed by the surfaces 257D and 257E of the locking tab 257 engages a corner of the second recess 216 preventing further movement of the lockable insert 250 toward the first end 211 of the collet sleeve 210. The surface 257E of the locking tab 257 extends past the second recess 216. The surface 257E locates inside the sidewall 212 of the collet sleeve 210 and makes contact with the inner surface 212B of the sidewall 212 to prevent upward movement of the live hinge 256 and locking tab 257. Therefore, the surface 257E facilitates maintaining radial compression around essentially the entire circumference of the collet 220. In the exemplary embodiment in which the locking tab 257 does not include the notch formed by the surfaces 257D and 257E, the abutment of the edge surface 215B against the edge surface 255B alone prevents further movement of the lockable insert 250 toward the first end 211 of the collet sleeve 210.

To transition from the first locking position to the second locking position, the collet sleeve 210 is slid toward the lockable insert 250, and the locking tab 257 travels from the first recess 214 to the second recess 216 along the guiding groove 217. Generally, when the locking apparatus 200 is in the first locking position, the live hinge 256 is in a relaxed state, i.e., it is not subject to bending forces. Thus, the locking tab 257 is disposed within the first recess 214. As the lockable insert 250 and the collet sleeve 210 are pressed toward one another, the sloped surface 257C of the locking tab 257 makes contact with the edge of the first recess 214 nearer to the first end 211. This contact causes the locking tab 257 to deflect radially toward the central axis 260. Thus, the live hinge 256 bends during the transition from the first locking position to the second locking position.

As the collet sleeve 210 continues to be pressed toward the lockable insert 250, the surface 257B of the locking tab 257 makes contact with a surface 219 of the sidewall 212 disposed between the first and second recesses 214 and 216. With continued pressing, the taper 254 of the lockable insert 250 then makes contact with the edge 226A of each resilient prong 222. The taper 254 acts as a wedge to radially compress the resilient prongs 222 inwardly toward the central axis 260 as the inner surface 252B and the taper 254 rides along the taper 226 of each prong 222. When the edge 257A of the locking tab 257 reaches the second recess 216, the locking tab 257 moves radially outwardly into the second recess 216 into the second locking position.

When the locking tab 257 of the lockable insert 250 is located in the second recess 216 of the collet sleeve 210, the lockable insert 250 radially compresses against the taper 226 of each of the plurality of resilient prongs 222, forcing the gripping surfaces 225 of the prongs 222 toward the center channel 218 and the central axis 260 of the collet sleeve 210. The gripping surfaces 225 of the collet 220 firmly compress against the catheter 300, which in turn compresses against the portion 410 of the stem 400, thereby securing the catheter 300 on the stem 400.

The inner diameter of the catheter 300 is less than the outer diameter of the portion 410 of the stem 400. The elasticity of the catheter 300 causes it to stretch over and uniformly compress on the portion 410 of the stem 400 when it is slipped onto the stem 400, thereby creating a seal that offers resistance to fluid leakage. The stem 400 includes a tapered portion 420 at its end to facilitate slipping the catheter 300 onto the stem 400. Thus, the locking apparatus 200 secures the catheter 300 to the stem 400 to prevent removal of the catheter 300 from the stem 400, while the catheter 300 remains stretched over and compressing against the stem 400 to resist fluid leakage. In an exemplary embodiment, the locking apparatus 200 also enhances the sealing capability between the catheter 300 and the stem 400.

When the locking tab 257 moves into position in the second recess 216, an operator of the locking apparatus 200 hears and feels a click indicating that the locking tab 257 is in place in the second locking position. This provides the operator a positive indication that the locking apparatus 200 is secured, and that the catheter 300 is secured to the stem 400. Relative movement of the lockable insert 250 and collet sleeve 210 during the locking process of the locking apparatus 200 can be equivalently described as pushing the collet sleeve 210 toward the lockable insert 250, or inserting the lockable insert 250 into the collet sleeve 210.

In the particular embodiment shown in FIG. 1, the second end 213 of the collet sleeve 210 is facing the exemplary implantable port 110. The orientation of the locking apparatus shown in FIG. 1 is for illustration only. The locking apparatus 200 can be used in the opposite orientation in which the second end 213 of the collet sleeve 210 faces away from the exemplary implantable port 110.

In a further exemplary embodiment, the collet sleeve 210 may also comprise an optional identification ring 212C formed in the outer surface 212A of the sidewall 212. The identification ring 212C may be color coded to indicate relevant information with regard to the locking apparatus 200, such as, without limitation, size, application, and manufacturing information.

Other embodiments of the lockable insert 250 are contemplated. For example, in another exemplary embodiment, the lockable insert 250 may incorporate an annular wall defining the center channel 258 that is tapered, i.e., the opening of the center channel 258 at the first end 251 is larger than the opening of the center channel 258 at the second end 253.

The present invention locking apparatus 200 is also suitable for a variety of stem designs and configurations. Traditionally, a connector for securing a flexible catheter to a stem generally requires one or more barbs or ribs on the stem. The locking apparatus 200 according to the present invention requires no such structural features on the stem, thereby simplifying stem design. However, the present invention locking apparatus 200 does not preclude including barbs or ribs or like features on the stem, and, in fact, can be used with such stems.

The exemplary collet sleeve 210 and the exemplary lockable insert 250 of the present invention locking apparatus 200 may be made from a plastic polymer. Preferably, a plastic polymer that provides the requisite elasticity that would facilitate the operation of the live hinge 256 and the plurality of resilient prongs 222 is used. The collet sleeve 210 and the lockable insert 250 may be made from the same or different materials. Suitable materials may include, without limitation, polyvinylchloride, polytetrafluoroethylene, polyethersulfone, polyethylene, polyurethane, polyetherimide, polycarbonate, polyetheretherketone, polysulfone, polypropylene, acetal plastic, and other similar compounds known to those skilled in the art. Preferably, the collet sleeve 210 and the lockable insert 250 are made by injection molding processes. One skilled in the art would appreciate that alternative choices of manufacturing processes may be available to carry out the functionality of the present invention locking apparatus.

These and other advantages of the present invention will be apparent to those skilled in the art from the foregoing specification. Accordingly, it will be recognized by those skilled in the art that changes or modifications may be made to the above described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. A locking apparatus for connecting a catheter to a stem of an implantable port, comprising:
   a collet sleeve comprising:
      a first end;
      a second end;
      a cylindrical wall defining a center channel extending from the first end to the second end of the collet sleeve; and
      at least one resilient prong protruding inward from the first end and extending into a portion of the center channel of the collet sleeve, each of the at least one resilient prong comprising a gripping surface facing the center channel; and
   a lockable insert comprising:
      a first end;
      a second end; and
      a cylindrical wall defining a center channel extending from the first end to the second end of the lockable insert, wherein the center channel of the lockable insert is coaxial with the center channel of the collet sleeve,
   wherein the lockable insert is configured to be placed at a first locking position at which the cylindrical wall of the lockable insert asserts no or minimal radial compression against the at least one resilient prong of the collet sleeve,
   wherein the lockable insert is further configured to be moved to a second locking position in which the lockable insert is prevented from returning to the first locking position and at which the cylindrical wall of the lockable insert radially compresses the at least one resilient prong of the collet sleeve so that the at least one resilient prong is deflected radially inwardly, and wherein the center channel of the collet sleeve and the center channel of the lockable insert are adapted to receive the stem of the implantable port and the catheter;

wherein the cylindrical wall of the collet sleeve further comprises:

a first recess; and a second recess, wherein the first recess of the cylindrical wall of the collet sleeve corresponds to the first locking position of the lockable insert, and wherein the second recess of the cylindrical wall of the collet sleeve corresponds to the second locking position of the lockable insert;

wherein the cylindrical wall of the lockable insert further comprises a locking tab adapted to engage the first and second recesses of the cylindrical wall of the collet sleeve;

wherein the cylindrical wall of the lockable insert further comprises a live hinge that couples the locking tab of the lockable insert to the cylindrical wall of the lockable insert.

2. The locking apparatus of claim 1, wherein the at least one resilient prong of the collet sleeve further comprises a tapered exterior surface.

3. The locking apparatus of claim 1, wherein the cylindrical wall of the collet sleeve further comprises a guiding groove extending at least between the first recess and the second recess.

4. The locking apparatus of claim 1, wherein the cylindrical wall of the lockable insert comprises an inner diameter and a taper in which the inner diameter of the cylindrical wall expands outwardly to the first end of the lockable insert.

5. A locking apparatus for connecting a catheter to a stem of an implantable port, comprising:

a sleeve comprising:
  a first end;
  a second end;
  a cylindrical wall defining a center channel extending from the first end to the second end of the sleeve; and
  a gripping surface; and a lockable insert, comprising:
  a first end;
  a second end; and
  a cylindrical wall defining a center channel extending from the first end to the second end of the lockable insert, wherein the center channel of the lockable insert is coaxial with the center channel of the sleeve, wherein the gripping surface is in an open state when not compressing the catheter against the stem of the implantable port and in a closed state when compressing the catheter against the stem of the implantable port, wherein the lockable insert is configured to be placed at a first locking position at which the gripping surface is in the open state, wherein the lockable insert is further configured to be moved to a second locking position in which the lockable insert is prevented from returning to the first locking position and at which the cylindrical wall of the lockable insert engages the gripping surface and the gripping surface is in the closed state, and wherein the center channel of the sleeve and the center channel of the lockable insert are adapted to receive the stem of the implantable port and the catheter.

6. The locking apparatus of claim 5, wherein the cylindrical wall of the sleeve further comprises:

a first recess; and a second recess, wherein the first recess of the cylindrical wall of the sleeve corresponds to the first locking position of the lockable insert, and wherein the second recess of the cylindrical wall of the sleeve corresponds to the second locking position of the lockable insert.

7. The locking apparatus of claim 6, wherein the cylindrical wall of the sleeve further comprises a guiding groove extending at least between the first recess and the second recess.

8. The locking apparatus of claim 7, wherein the cylindrical wall of the lockable insert further comprises a locking tab adapted to engage the first and second recesses of the cylindrical wall of the sleeve.

9. The locking apparatus of claim 5, wherein the cylindrical wall of the lockable insert comprises an inner diameter and a taper in which the inner diameter of the cylindrical wall expands outwardly to the first end of the lockable insert.

* * * * *